(12) United States Patent
Lentner et al.

(10) Patent No.: US 10,022,239 B1
(45) Date of Patent: Jul. 17, 2018

(54) SPINAL IMPLANT WITH OPPOSING TAPER COAXIAL DRIVE SYSTEM

(71) Applicant: Hammill Medical LLC, Palm Beach Gardens, FL (US)

(72) Inventors: Greg Lentner, Maumee, OH (US); John E. Hammill, Sr., Maumee, OH (US)

(73) Assignee: Hammill Medical LLC, Palm Beach Gardens, FL (US)

( * ) Notice: Subject to any disclaimer, the term of this patent is extended or adjusted under 35 U.S.C. 154(b) by 0 days.

(21) Appl. No.: 15/827,735

(22) Filed: Nov. 30, 2017

Related U.S. Application Data

(60) Provisional application No. 62/546,219, filed on Aug. 16, 2017.

(51) Int. Cl.
  *A61F 2/44* (2006.01)
  *A61F 2/46* (2006.01)
  *A61F 2/30* (2006.01)

(52) U.S. Cl.
  CPC ............ *A61F 2/4425* (2013.01); *A61F 2/447* (2013.01); *A61F 2/4611* (2013.01); *A61F 2/4637* (2013.01); *A61F 2002/30525* (2013.01); *A61F 2002/30579* (2013.01); *A61F 2002/443* (2013.01); *A61F 2002/4623* (2013.01); *A61F 2002/4627* (2013.01); *A61F 2002/4638* (2013.01)

(58) Field of Classification Search
  CPC .. A61F 2002/30266; A61F 2002/30471; A61F 2/447
  See application file for complete search history.

(56) References Cited

U.S. PATENT DOCUMENTS

| | | | |
|---|---|---|---|
| 9,566,168 B2* | 2/2017 | Glerum | A61F 2/442 |
| 2004/0087947 A1* | 5/2004 | Lim | A61F 2/4465 606/247 |
| 2006/0253201 A1* | 11/2006 | McLuen | A61F 2/4455 623/17.15 |
| 2008/0140207 A1* | 6/2008 | Olmos | A61F 2/447 623/17.16 |
| 2013/0006361 A1* | 1/2013 | Glerum | A61F 2/4455 623/17.16 |
| 2013/0158664 A1* | 6/2013 | Palmatier | A61F 2/447 623/17.16 |
| 2013/0211526 A1* | 8/2013 | Alheidt | A61F 2/4611 623/17.16 |

(Continued)

*Primary Examiner* — Jacqueline Johanas
(74) *Attorney, Agent, or Firm* — McHale & Slavin, P.A.

(57) ABSTRACT

An opposing taper coaxial spinal implant. The system consists of a centrally located drive screw with opposing lead threads and actuators. The actuators contain pins positioned through angular slots located on sidewalls attached to end plates. The angular slots are opposing to create a wedge effect when the actuator pins translate through them. A carriage contains a drive screw and centrally located pin. The centrally located pin provides axis to contain each end plate, allowing them to pivot and translate relative to the carriage. An adjustment nut is axially retained by the carriage, but allowed to rotate. To expand/contract the end plates, the drive screw and adjustment nut are rotated together, with no relative motion between them. To change the angle of the end plates, the adjustment nut is rotated while keeping the drive screw rotation fixed.

11 Claims, 18 Drawing Sheets

(56) References Cited

U.S. PATENT DOCUMENTS

| | | | | |
|---|---|---|---|---|
| 2014/0257484 A1* | 9/2014 | Flower | ............... | A61F 2/447 |
| | | | | 623/17.15 |
| 2016/0213482 A1* | 7/2016 | Alheidt | ............... | A61F 2/4611 |
| 2017/0281361 A1* | 10/2017 | Jimenez | ............... | A61F 2/447 |
| 2017/0304071 A1* | 10/2017 | Black | ............... | A61F 2/4425 |
| 2017/0333198 A1* | 11/2017 | Robinson | ............... | A61F 2/447 |
| 2017/0367842 A1* | 12/2017 | Predick | ............... | A61F 2/447 |

\* cited by examiner

SECTION A-A

SECTION A-A

SECTION A-A

SECTION A-A

SPINAL IMPLANT WITH OPPOSING TAPER COAXIAL DRIVE SYSTEM

PRIORITY CLAIM

In accordance with 37 C.F.R. § 1.76, a claim of priority is included in an Application Data Sheet filed concurrently herewith. Accordingly, the present invention claims priority to U.S. Provisional Patent Application No. 62/546,219 entitled "OPPOSING TAPER COAXIAL DRIVE SYSTEM", filed Aug. 16, 2017. The contents of which the above referenced application is incorporated herein by reference.

FIELD OF THE INVENTION

This invention is directed to the field of spinal implants, namely a spinal implant with an opposing taper coaxial drive system.

BACKGROUND OF THE INVENTION

Back pain affects every human to some extent. Causes of back pain can result from a number of issues, one of which is the rupture or degeneration of intervertebral discs due to aging, disease, himation, or trauma. Left untreated, the failure of a disc can lead to compression on the spinal cord or cauda equian. Many types of spinal irregularities can cause pain, limit range of motion, or injure the nervous system within the spinal column. These irregularities can leave the individual with numbness, pain, weakness or in a state of permanent disability.

Spinal stabilization is an accepted method in alleviating chronic back pain caused by disabled disk material or excessive movement of individual vertebrae. Conventional stabilization techniques include fusing two or more vertebrae together to circumvent or immobilization of the area to eliminate disc movement. Generally, spinal fusion procedures involve removing some or the all of the diseased or damaged disc, and inserting one or more intervertebral implants into the resulting disc space. Many irregularities can be treated by immobilizing the failing disc or performing a discectomy. For example, treatment can include removal and replacement of an affected intervertebral disc with a prosthesis. For instance, the vertebral disk material which separates the vertebrae can be removed and bone graft material is inserted in the space for interbody fusion. In addition to, or in place of, the bone graft material, a spinal implant may be inserted in the intervertebral space.

In certain applications it is beneficial that a device is used which is capable of fitting within a confined space, wherein the device can be further adjusted in height and angular adjustment from one end to the other. The ability to adjust the height and angular tilt must be accessible while the device is mounted.

SUMMARY OF THE INVENTION

Disclosed is an opposing taper coaxial spinal implant consisting of a centrally located drive screw with opposing lead threads on either side. The drive screw has actuators with matching threads on either side of the center of the drive screw. The actuators contain pins which are positioned through angular slots located in each end plate. The angular slots in each end plate are opposing, which creates a wedge effect when the actuator pins translate through them. A carriage contains the drive screw and actuators, and houses a pair of centrally located fixed pins. The pins create an axis to contain each end plate and allow them to pivot and translate relative to the carriage. An adjustment nut is situated at the end of the carriage and threaded on the drive screw. The nut is axially retained by the carriage, but allowed to rotate. To expand/contract the end plates, the drive thread and adjustment nut are rotated together with no relative motion between them. To change the angle of the end plates, the adjustment nut is rotated while keeping the drive screw rotation fixed.

An objective of the invention is to teach a device to fit in a confined space with height adjustment and angular adjustment from one end to the other.

Another objective of the invention is to teach a device for insertion into a confined space, wherein the height of the device is adjusted by rotation of a drive screw and angular adjustment of the device is adjusted by rotation of an adjustment nut.

Still another objective of the invention is to provide a mechanism for height and angular adjustment from one an end of the device.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE PREFERRED EMBODIMENT

Figure 1:
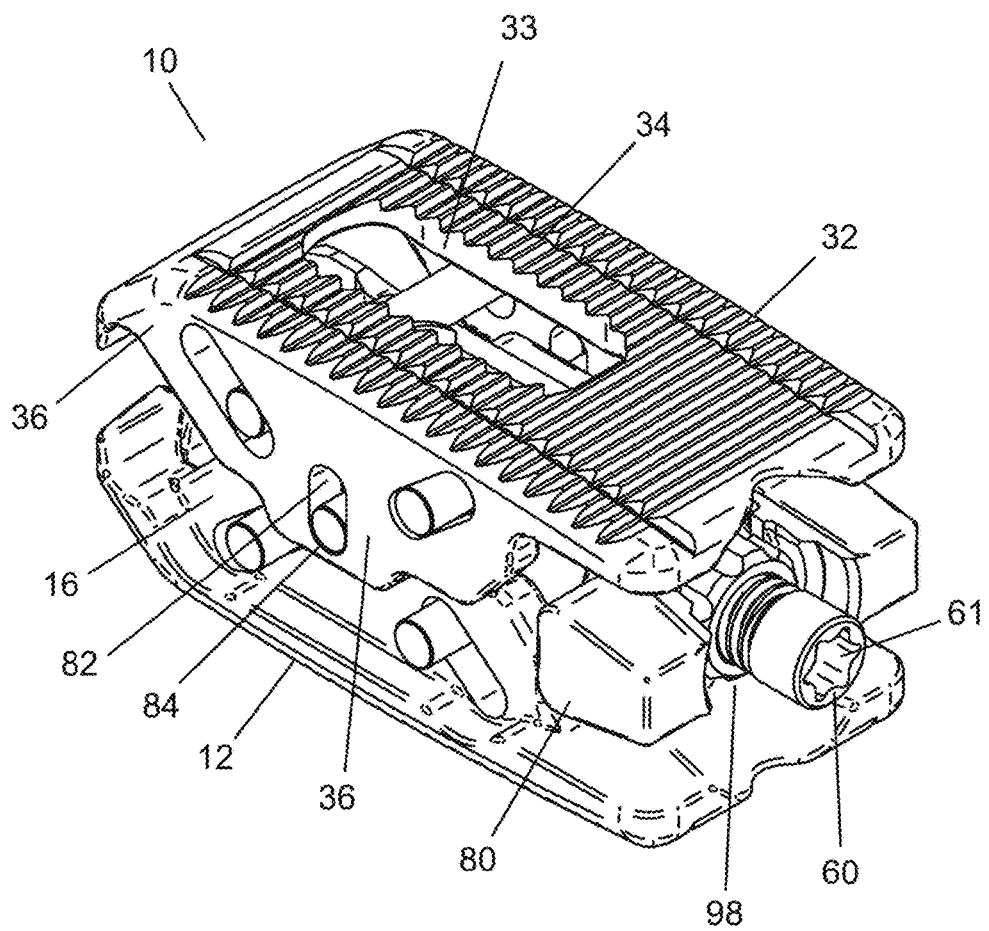
FIG. 1 is a perspective view of the spinal implant.
Figure 2:
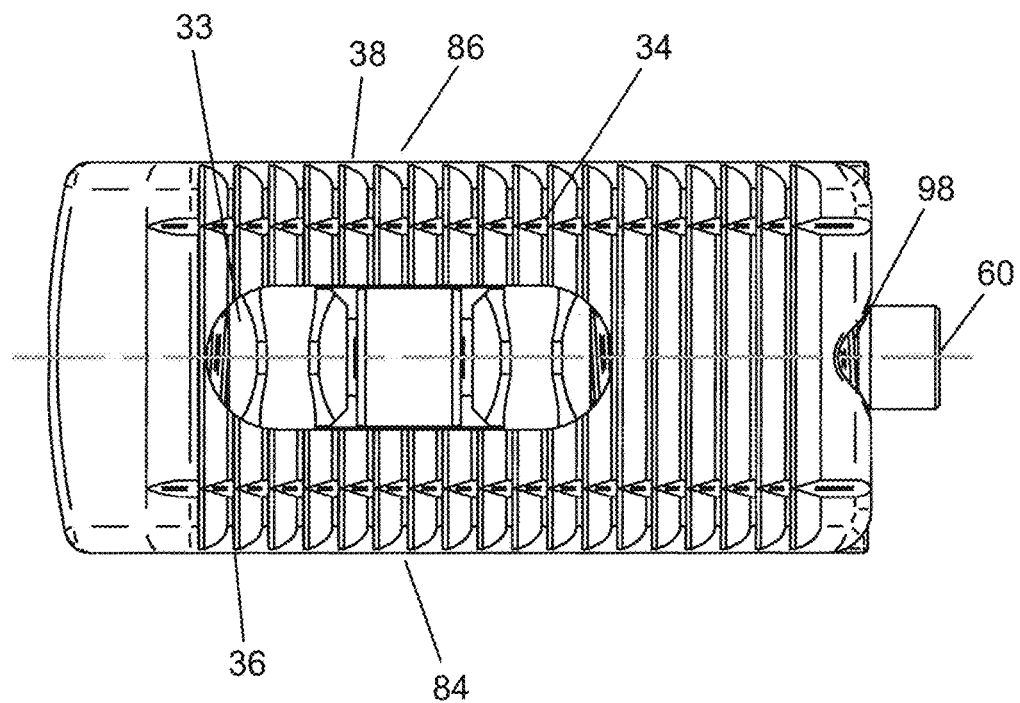
FIG. 2 is a top view of the spinal implant.
Figure 3:
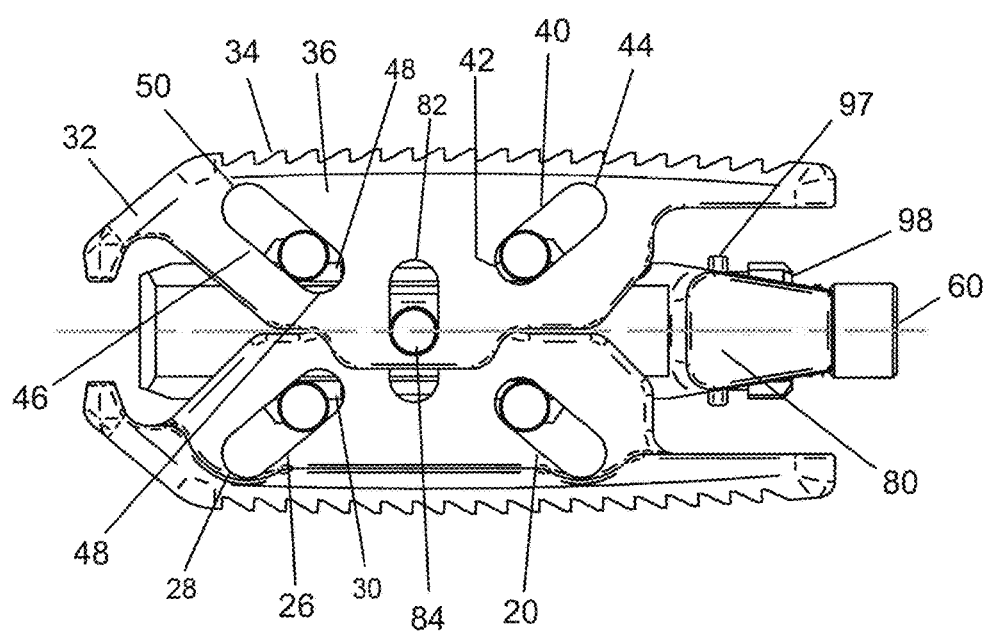
FIG. 3 is a side view thereof in a parallel expanded position.
Figure 4:
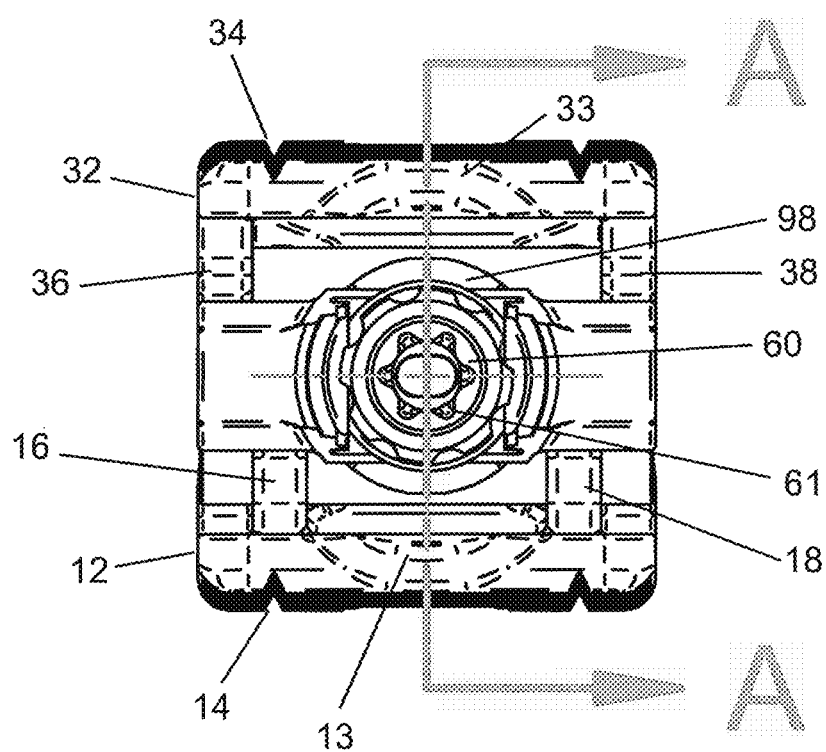
FIG. 4 is an end view of the spinal implant.

Referring to the Figures, the opposing taper coaxial spinal implant 10 consists of a substantially rectangular bottom endplate 12 having a grooved outer surface 14 to engage bone and a first vertical inner sidewall 16 spaced apart from a second inner vertical sidewall 18 placed in a parallel position. The first inner vertical sidewall 16 has a front bottom slot 20 placed at a predetermined angle defined by a lower end 22 and an upper end 24, and a rear bottom slot 26 placed at a predetermined angle defined by a lower end 28 and an upper end 30. Lower ends 22 and 28 of the slots 20 and 26 are positioned farther apart than the upper ends 24 and 30 of the slots 20 and 26, which defines the angular slope. The second inner sidewall 18 forms a mirror image of the first inner sidewall 16, including a front and rear bottom slot with the same angular slope as the first inner sidewall 16.

A top endplate 32 having a grooved outer surface 34 and a first outer vertical sidewall 36, and a second outer vertical sidewall 38 depending therefrom and placed in a parallel position spaced apart from the first outer vertical sidewall 36 to allow nesting with the sidewalls 16 and 18 of said bottom endplate 12. The first outer vertical sidewall 36 has a front slot 40 placed at a predetermined angle defined by a lower end 42 and an upper end 44, and a rear slot 46 placed at a predetermined angle defined by a lower end and an upper end 50. Lower ends 42 and 48 are positioned closer together than the upper ends 44 and 50, which defines an angular slope. The second outer vertical sidewall 38 forms a mirror image of the first outer vertical sidewall 36, including a front and rear slot with the same angular slope as the first outer vertical sidewall 36. In the preferred embodiment, each of the angled slots are angled at about 45 degrees. However, the angle can be between 25 and 75 degrees for use with targeted applications. Bottom endplate 12 may include an aperture 13, and top endplate 32 may include aperture 33 for receipt of bone or bone graft material.

A centrally located drive screw 60 with opposing lead threads 62 and 64 is located on either side of a center section 66. The opposing lead threads are formed clockwise and counterclockwise. The drive screw 60 has a front threaded actuator 68 moved by lead thread 64 with matching threads and rear threaded actuator 70 moved by lead thread 62. Front actuator 68 contains upper pin 72 positioned above a carriage 80 and lower pin 74 positioned beneath the carriage 80, the upper and lower pins 72, 74 are positioned in the angular slots 40 and 20 respectively. Similarly, rear actuator 70 contains upper pin 76 and lower pin 78, which are positioned through the angular slots 46 and 26 respectively. The angular slots in each end plate are opposing and sloped to allow parallel positioning of the endplates or angular positioning thereof.

A carriage 80 contains the drive screw 60 and supports the actuators 68 and 70. The carriage 80 has a centrally disposed aperture and includes a first centrally located pin 84 that extends outward from a first side of said carriage for placement though a vertical slot 82 formed in the first outer vertical sidewall 36 of top endplate 32 and the first inner vertical sidewall 16 of the bottom endplate 12. A second centrally located pin 86 extends outward from a second side of said carriage for placement through a vertical slot 85 formed in the second outer vertical sidewall 38 of top endplate 32 and the second inner vertical sidewall 18 of the bottom endplate 12. The position pins 84 and 86 form a rotational point in respect to the sidewalls and allow them to pivot and translate vertically relative to the carriage 80. The opposing pin 86 operates the same way to support the second inner 18 and said outer 38 sidewall along vertical slots 85 and 87.

The carriage 80 is comprised of a frontal portion 90 and a rear portion 92. The drive screw 60 is attached to the frontal portion 90 where it is allowed to freely rotate. Star socket 61 is sized to receive a driver for ease of rotation. Adjustment nut 98 is situated at the frontal portion 90 of the carriage 80 wherein a portion of the adjustment nut is held to the carriage to prevent axial movement yet allow rotational movement. The adjustment nut 98 is threaded for receipt of the drive screw 60. The adjustment nut 98 has a lip 97 which engages a tab 99 formed in the carriage 80 wherein rotation of the adjustment nut 98 causing axial translation of the drive screw 60 yet maintaining a position against the carriage 80 as provided by the tab 99.

Figure 5:
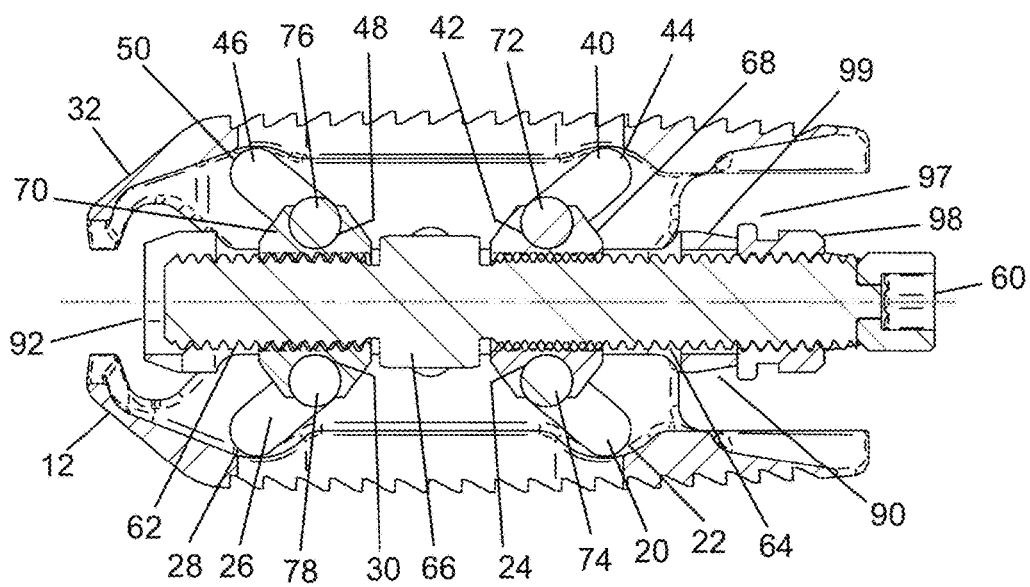
FIG. 5 is a cross sectional view of the spinal implant in a parallel expanded position.
Figure 6:
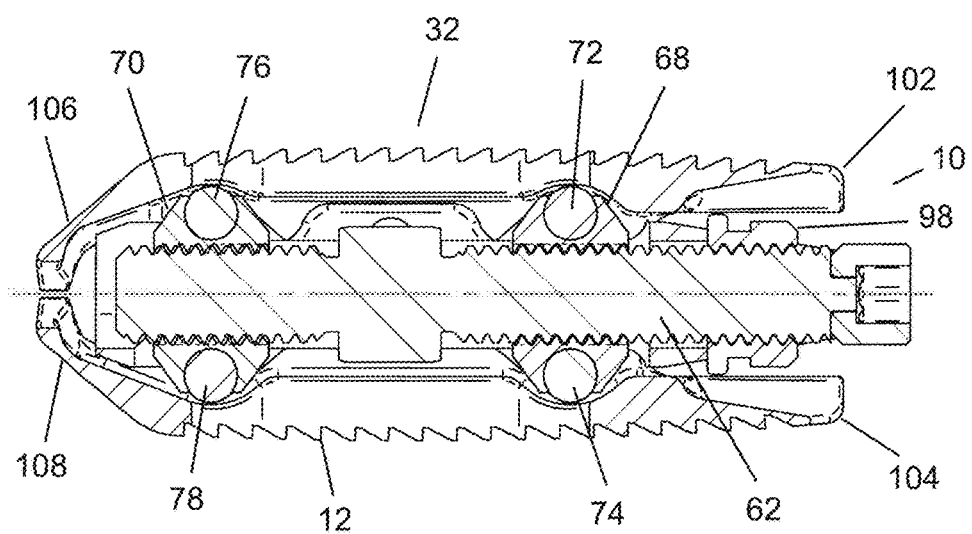
FIG. 6 is a cross sectional side view of the spinal implant in a contracted position.

To evenly expand or contract the end plates 12 and 32, as depicted in FIG. 5, the drive screw 60 and adjustment nut 98 are rotated together, with no relative motion between them. To change the angle of the end plates 12 and 32, as depicted in FIG. 6, the adjustment nut 98 is rotated while keeping the drive screw 60 fixed, or the drive screw 60 can be rotated keeping the adjustment nut fixed. Whereby rotation of the drive screw 60 moves the actuators in unison wherein the pins engage the slots to cause equal separation of the bottom and top endplates. Rotation of the adjustment nut repositions the drive screw 60 in respect to the carriage wherein the pins 72, 74, 76, & 78 engage the slots 40, 20, 46 and 24 resulting in angular positioning of the bottom 12 and top 32 endplate.

Figure 7:
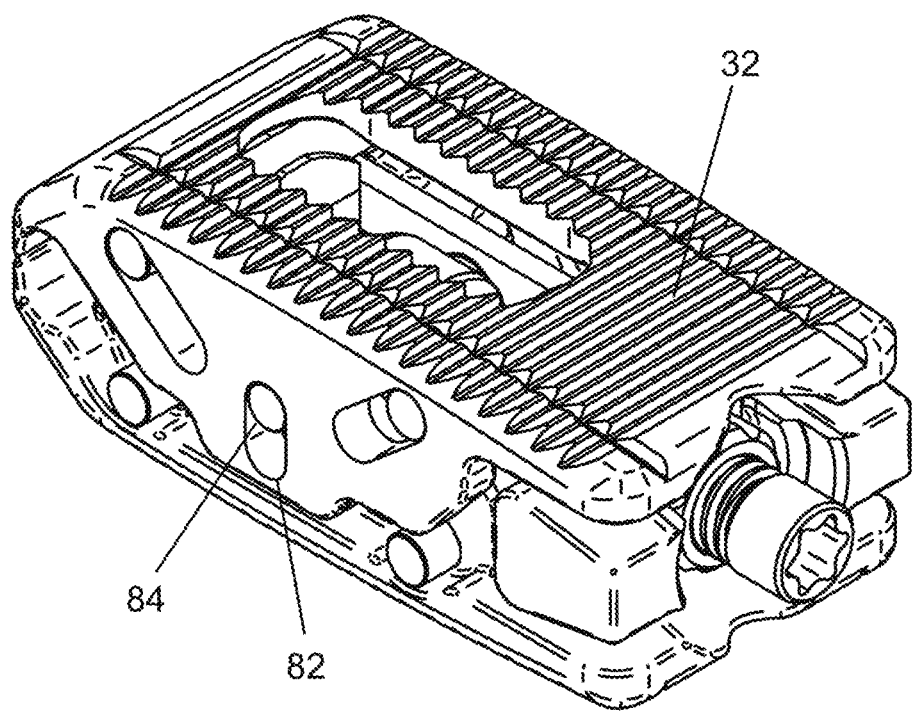
FIG. 7 is a perspective view of the spinal implant in a contracted position.

FIGS. 6 and 7 depict the spinal implant in a contracted position. In this depiction the actuators 68, 70 are centered on the drive screw 60, and the drive screw 60 has been rotated to a position where the upper pins 76, 78 are located at the top of the outer slots 46, 40. Lower pins 74, 78 are located at the bottom of the inner slots 20, 26. The center pin 84 is located along the top of the vertical slot 82. For simplicity, the slots and pins are shown on one side of the implant, the opposite side forming a mirror image.

Figure 8:
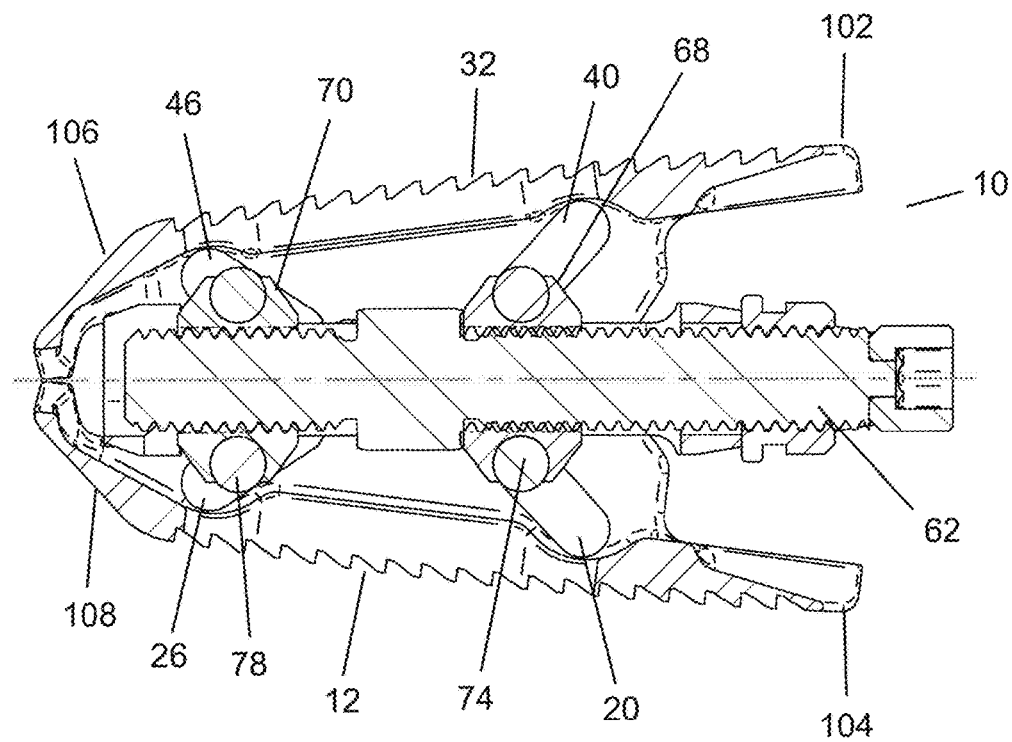
FIG. 8 is a cross sectional side view of the spinal implant in a anterior tilt position.
Figure 9:
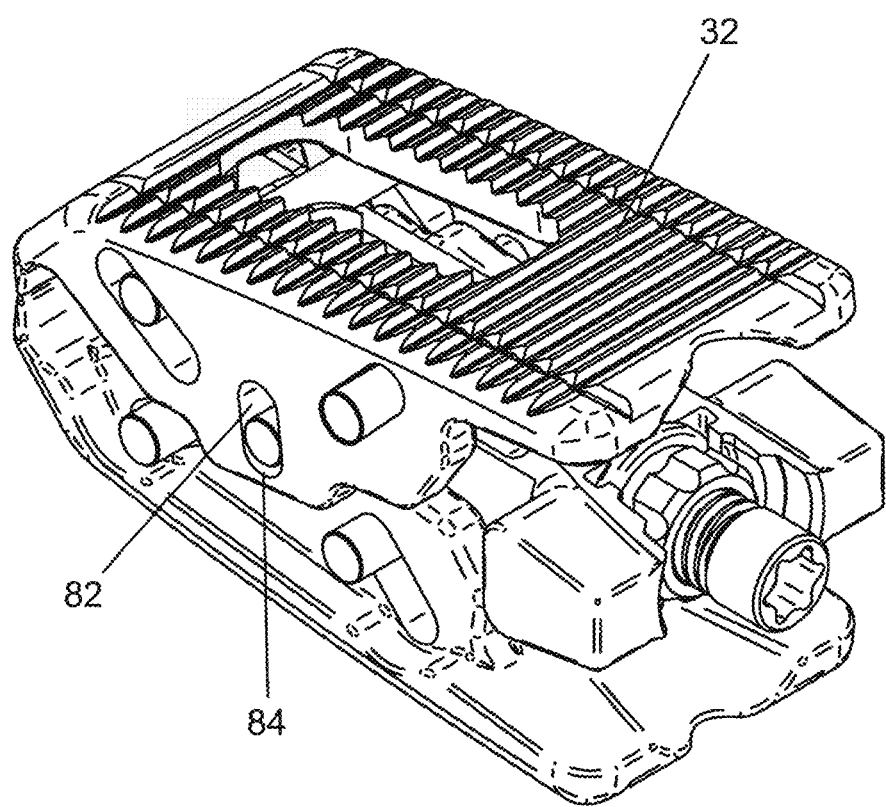
FIG. 9 is a perspective view of the spinal implant in the anterior tilt position.

FIGS. 8 and 9 depict the spinal implant 10 in a anterior tilt position. In this depiction the forward actuator 68 is moved toward the center of the drive screw 60 causing the front edges 102, 104 of the endplates 12, 32 to separate and maintaining the rear edges 106, 108 of the endplates 12, 32 to be a closed position. The separation is caused by rotation of the adjustment nut 98 and the drive screw 60. The center pin 84 is located along the middle of the vertical slot 82.

Figure 10:
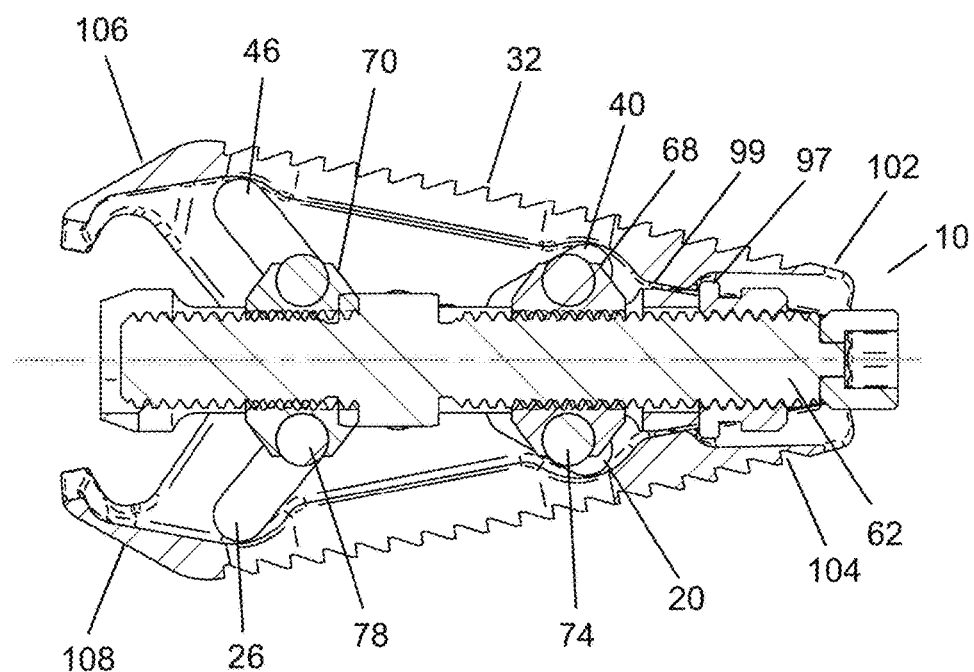
FIG. 10 is a cross sectional side view of the spinal implant in a posterior tilt position.
Figure 11:
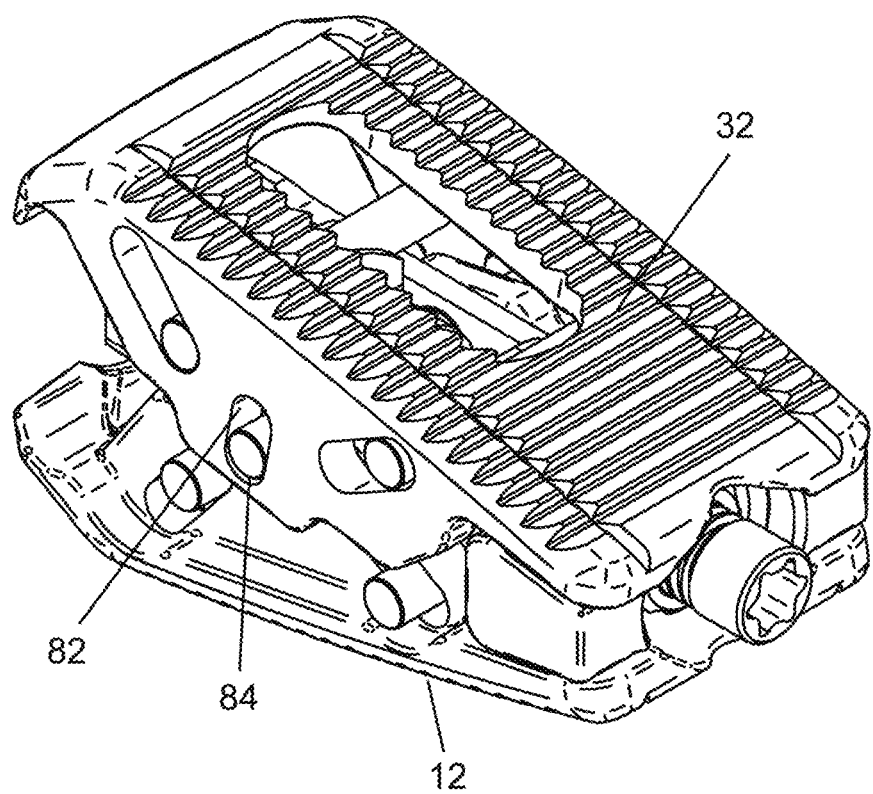
FIG. 11 is a perspective view of the spinal implant in the posterior tilt position.
Figure 12:
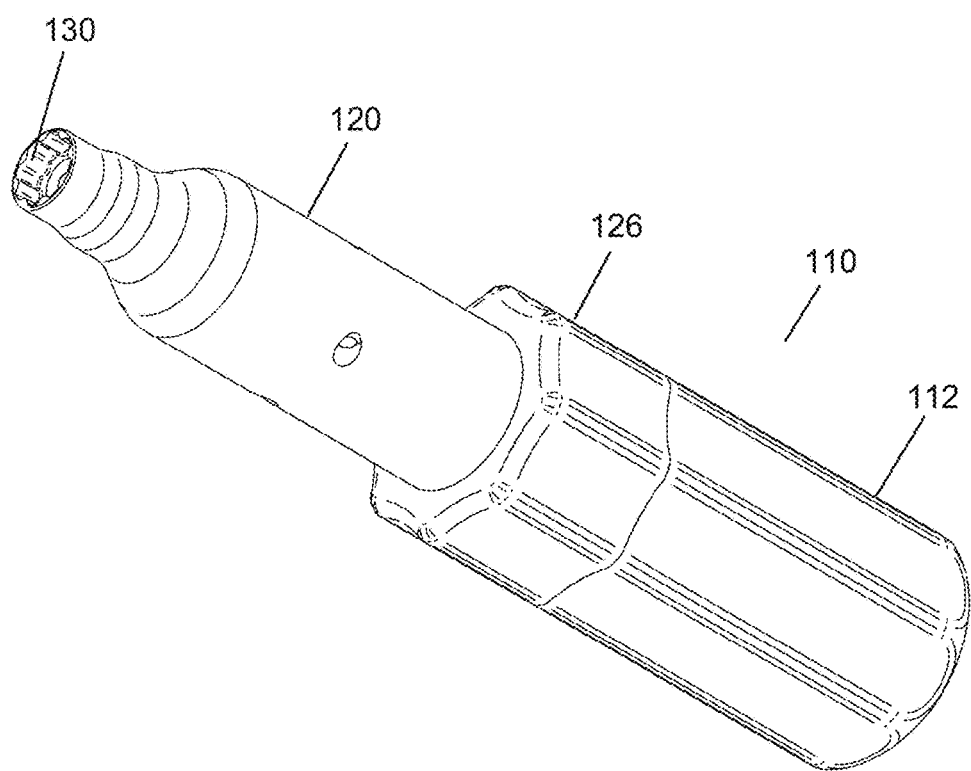
FIG. 12 is a perspective view of the instrument driver.
Figure 13:
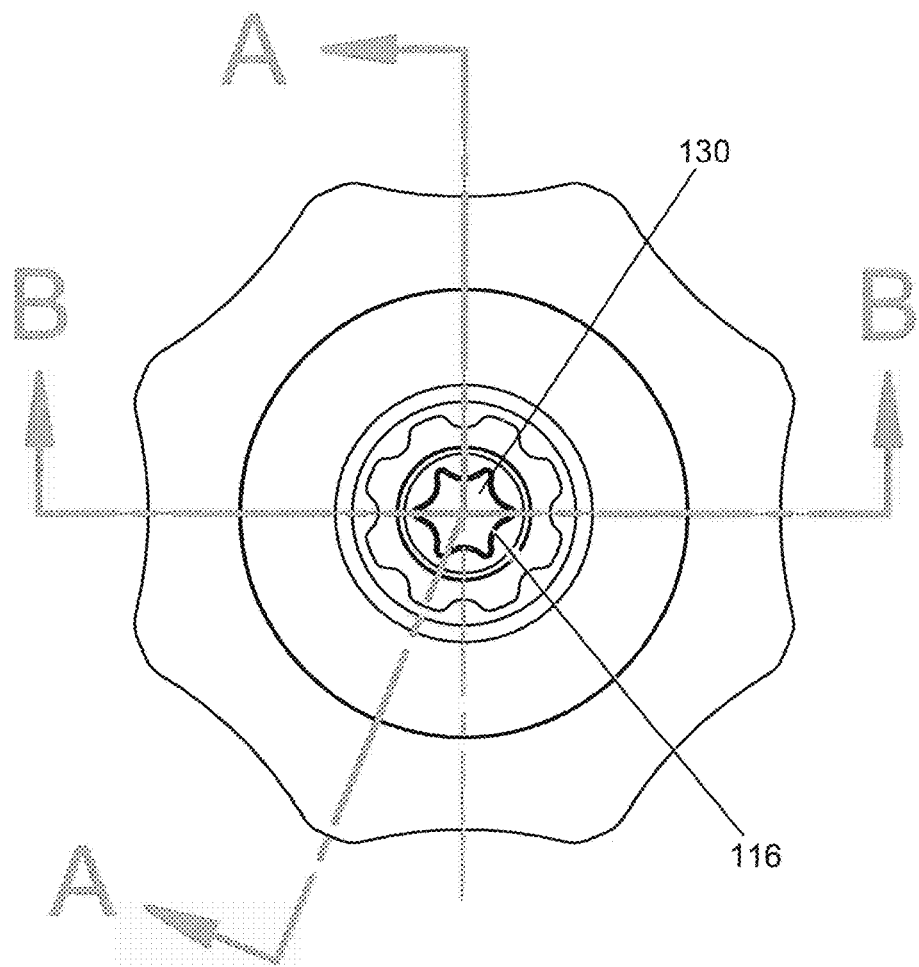
FIG. 13 is an end view of the instrument driver.
Figure 14:
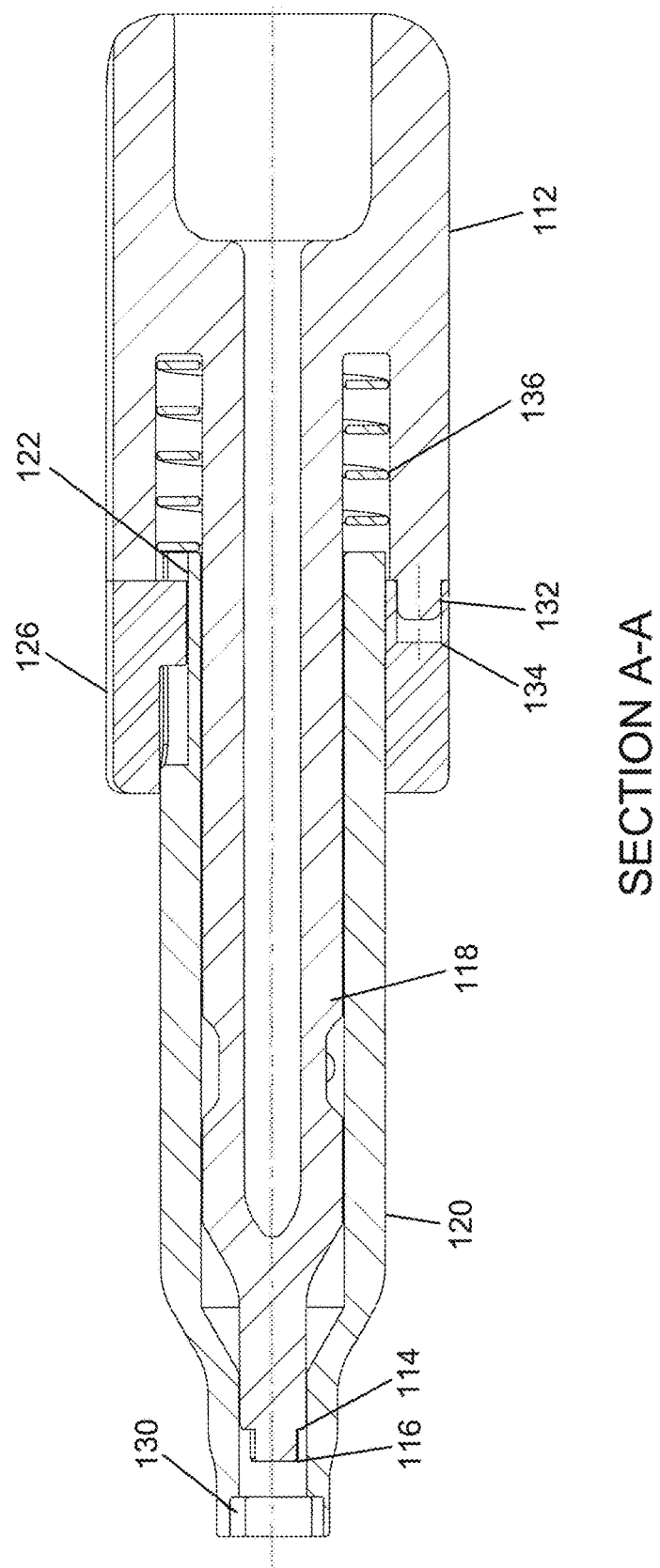
FIG. 14 is a cross sectional side view taken along Section lines A-A.

FIGS. 10 and 11 depict the spinal implant 10 in a posterior tilt position. In this depiction the forward actuator 68 is moved toward the front end of the drive screw 60 and the rear actuator 70 is moved toward the center of the drive screw 60. The location of the actuators 68, 70 cause the front edges 102, 104 of the endplates 12, 32 to be a close position and the back ends 106, rear edges of the endplates 12, 32 to be in a separated position. The seperation is caused by rotation of the adjustment nut 98 and the drive screw 60. The center pin 84 is located along the bottom of the vertical slot 82. The spinal implant of the present invention may be comprised of any suitable non-bone composition, including but not limited to metal, polymer compositions (e.g. poly-ether-ether-ketone (PEEK) and/or poly-ether-ketone-ketone (PEKK)), ceramic, or any combination of these materials.

Referring now to FIGS. 12-18, illustrated is the instrutment driver 110 for use in installing the implant 10. The instrument driver 110 engages the star socket 61 of the drive screw 60 and adjustment nut 98, wherein the drive screw 60 and adjustment nut 98 can be rotated simultaneously or independently adjusting the height and angular position of the endplates 12, 32. The driver 110 is formed from a base 112 sized to allow gripping by an individual on one end and a driver head 114 connected thereto having a star tip driver 116 for rotating of the drive screw star socket 61. In the preferred embodiment, the base 112 and shaft 118 are connected to assure rotational movement is one piece. An extendable sleeve 120 having a proximal end 122 is slidably securable to the 112 using a slide collar 126. The slide collar 126 engages the base 112 to allow simultaneous rotation of an adjustment nut socket 130 when the slide collar 126 engages the base 112. When the slide collar 126 is detached from the base 112, only the base 112 is engaged to cause rotation of the star tip driver 116. The base 112 has a plurality of engagement tabs 132 to interlock with receptacles 134 located along the perimeter of the slide collar 126. The slide collar 126 having at least one spring 134 to bias the slide collar 126 with the base 112.

Figure 15:
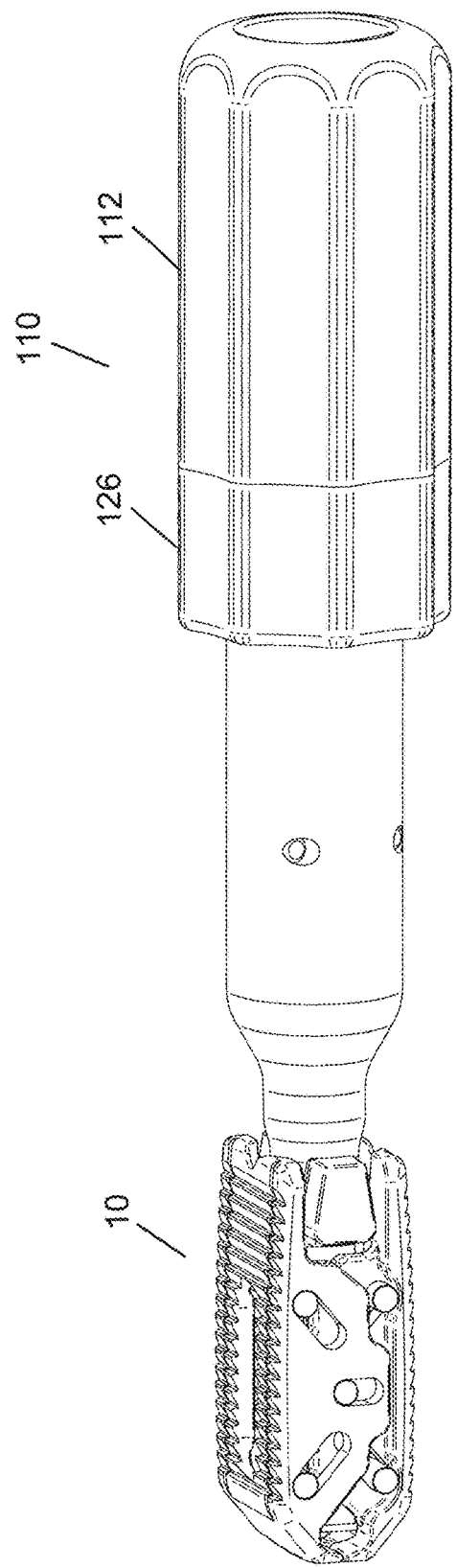
FIG. 15 is a pictorial view depicting the instrument driver engaging a spinal implant in a closed position.
Figure 16:
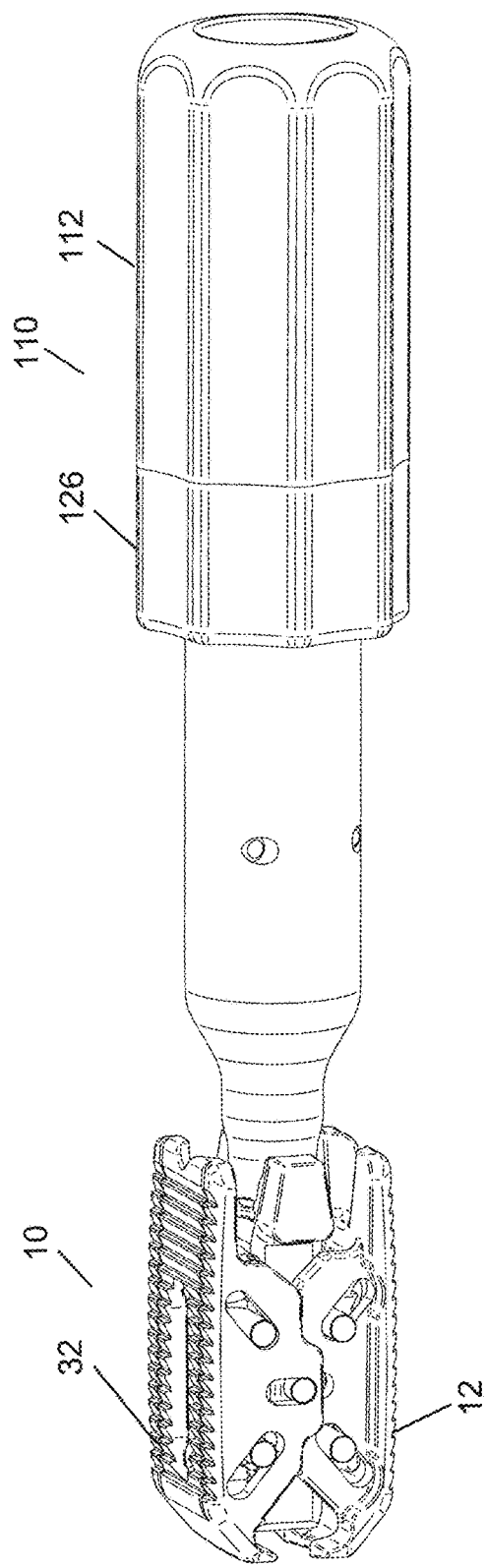
FIG. 16 is a pictorial view depicting the instrument driver engaging a spinal implant in an open position.

FIG. 15 is a pictorial view depicting the instrument driver 110 engaging a spinal implant 10 in a closed position. The slide collar 126 is adjacent the base 112 wherein the star tip driver and adjustment nut socket would rotate in unison allow the implant to expand as depicted in FIG. 16 causing uniform seperation of bottom endplate 12 to top endplate 32.

Figure 17:
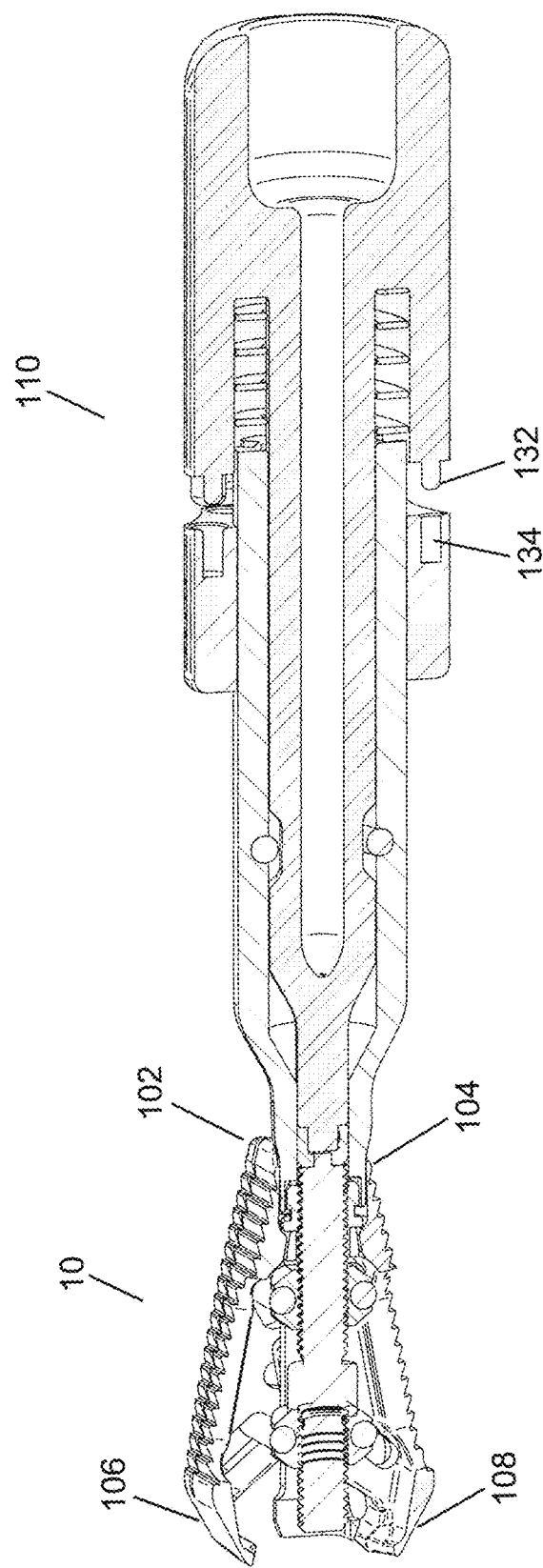
FIG. 17 is a cross sectional view depicting the instrument driver providing frontal angular adjustment to the spinal implant.
Figure 18:
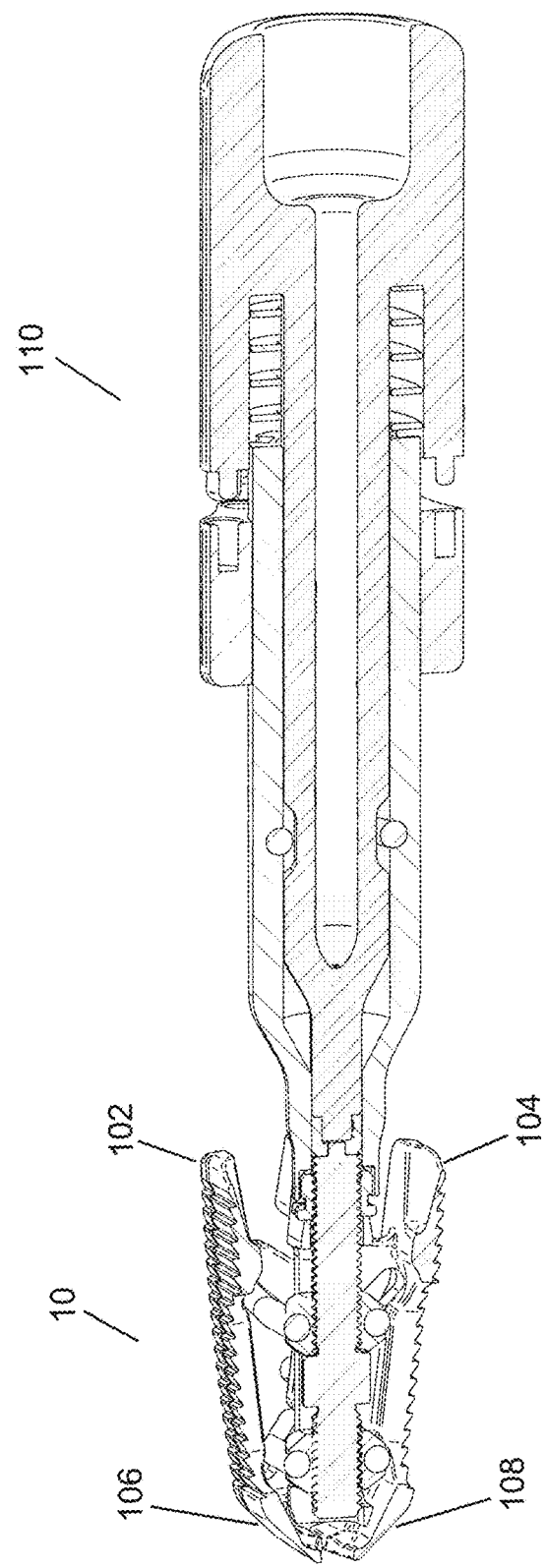
FIG. 18 is a cross sectional pictorial view depicting the instrument driver providing rearward angular adjustment to the spinal implant.

FIG. 17 is a cross sectional view depicting the instrument driver 110 providing frontal angular adjustment to the spinal implant 10. In this depiction the slide collar 126 is separated from the base 112 disengaging the tabs 132 from the receptacle 134. In this illustration the adjustment nut socket 130 is separated from the star driver 116 and allowed to rotate independently. Rotation of the base 110 results in the forward adjustment of the implant wherein the forward edges 102, 104 remain in a closed position and the rearward edges 106, 108 are expanded. Reversal of the base 110 results in the opposite rotation causing forward edges 106 and 108 to close and forward edges 102 and 104 to open. The tool allows a surgeon the ability to adjust the height and angular slope of the endplates 12, 32.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An opposing taper coaxial spinal implant system comprising:
a substantially rectangular bottom endplate having a first inner vertical sidewall extending from a front edge to a rear edge of said bottom endplate and a second inner vertical sidewall spaced apart from said first inner vertical sidewall, each said inner vertical sidewall including a front angled slot, a rear angled slot, and a centrally disposed vertical slot;
a substantially rectangular top endplate having a first outer vertical sidewall extending from a front edge to a rear edge of said top endplate and a second outer vertical sidewall spaced apart from said first outer vertical sidewall, each said outer vertical sidewall including a front angled slot, a rear angled slot, and a centrally disposed vertical slot;
a carriage having a threaded aperture, said carriage positionable between said inner and outer vertical sidewalls with a centrally disposed pin positioned in each of said vertical slot of said inner sidewalls and said outer sidewalls;
a drive screw rotatably insertable into said carriage aperture, said drive screw having clockwise threads along a first portion and counterclockwise threads along a second portion;
a first actuator threadably attached to said first portion of said drive screw, said first actuator having a front lower pin extending across a lower surface of said carriage, said front lower pin operatively associated with said front angled slot in said inner sidewalls of said bottom endplate, said first actuator having a front upper pin extending across an upper surface of said carriage with said front upper pin operatively associated with said front angled slot in said outer sidewalls of said top endplate;
a second actuator threadably attached to said second portion of said drive screw, said second actuator having a rear lower pin extending across the lower surface of said carriage, said rear lower pin operatively associated with said rear angled slot in said inner sidewalls of said bottom endplate and a rear upper pin operatively associated with said rear angled slot in said outer sidewalls of said top endplate; and
an adjustment nut rotatably secured to said carriage, said adjustment nut threadingly attached to the drive screw;
whereby simultaneous rotation of said drive screw and said adjustment nut moves said actuators in unison wherein said pins engage said slots to cause equal separation of said bottom and top endplates;
whereby rotation of said adjustment nut without said drive screw rotation repositions said screw drive in respect to said carriage wherein said pins engage said slots to cause an angular positioning of said bottom and top endplates.

2. The opposing taper coaxial spinal implant system according to claim 1 wherein rotation of said adjustment nut in a clockwise position expands the distance between frontal edges of said bottom endplate and said top endplate.

3. The opposing taper coaxial spinal implant system according to claim 1 wherein rotation of said adjustment nut in a counter clockwise position expands the distance between rearward edges of said bottom endplate and said top endplate.

4. The opposing taper coaxial spinal implant system according to claim 1 wherein said rear edge of said bottom endplate and said top endplate includes a sloped outer surface.

5. The opposing taper coaxial spinal implant system according to claim 1 wherein an outer surface of each said endplate has a plurality of grooves constructed and arranged to engage bone.

6. The opposing taper coaxial spinal implant system according to claim 5 wherein each said outer surface of each said endplate includes an aperture for receipt of bone or bone graft material.

7. The opposing taper coaxial spinal implant system according to claim 5 wherein said angled slots in said inner sidewalls are about 45 degrees relative to the outer surface of said bottom endplate.

8. The opposing taper coaxial spinal implant system according to claim 5 wherein said angled slots in said outer sidewalls are about 45 degrees relative to the outer surface of said top endplate.

9. The opposing taper coaxial spinal implant system according to claim 1 wherein said angled slots are sloped toward said centrally disposed pin.

10. The opposing taper coaxial spinal implant system according to claim 1 wherein said drive screw has a star driver receptacle.

11. The opposing taper coaxial spinal implant system according to claim 1 wherein in said drive screw and adjustment nut can be rotated simultaneously or independently by an instrument driver comprising:
   a handle having formed from a base to allow gripping by an individual on one end and a driver head for rotating of said drive screw on an opposite end;
   an extendable sleeve having a proximal end slidably securable to said base using a slide collar, said slide collar engaging said handle to allow simultaneous rotation of said adjustment nut and said drive screw when said slide collar is attached to said base, said base to allow only rotation of said adjustment nut when said collar is detached from said base.

* * * * *